United States Patent
Weichert et al.

[11] Patent Number: 6,156,800
[45] Date of Patent: Dec. 5, 2000

[54] 4-FLUOROALKYL-SUBSTITUTED BENZOYLGUANIDINES, PROCESS FOR THEIR PREPARATION, THEIR USE AS A MEDICAMENT OR DIAGNOSTIC, AND MEDICAMENT CONTAINING THEM

[75] Inventors: Andreas Weichert, Egelsbach; Joachim Brendel, Bad Vilbel; Heinz-Werner Kleemann, Bischofsheim; Hans Jochen Lang, Hofheim; Jan-Robert Schwark, Kelkheim; Wolfgang Scholz, Eschborn; Udo Albus, Florstadt, all of Germany

[73] Assignee: Aventis Pharma Deutschland GmbH, Frankfurt am Main, Germany

[21] Appl. No.: 09/108,126

[22] Filed: Jun. 22, 1998

Related U.S. Application Data

[63] Continuation of application No. 08/679,550, Jul. 12, 1996, abandoned.

[30] Foreign Application Priority Data

Jul. 19, 1995 [DE] Germany .......................... 195 26 381

[51] Int. Cl.[7] ....................... A61K 31/165; C07C 279/22
[52] U.S. Cl. ........................... 514/618; 514/309; 514/312; 514/345; 514/398; 514/424; 546/134; 546/141; 546/290; 548/335.1; 548/541; 564/134; 564/162; 564/237
[58] Field of Search ..................................... 514/618, 309, 514/312, 345, 398, 424; 564/134, 162, 237; 548/335.1, 541; 546/134, 141, 290

[56] References Cited

U.S. PATENT DOCUMENTS

| | | |
|---|---|---|
| 3,780,027 | 12/1973 | Cragoe et al. . |
| 5,091,394 | 2/1992 | Englert et al. . |
| 5,373,024 | 12/1994 | Lang et al. . |

FOREIGN PATENT DOCUMENTS

| | | |
|---|---|---|
| B-55229/94 | 8/1994 | Australia . |
| 71507/94 | 3/1995 | Australia . |
| 0612723 A1 | 8/1994 | European Pat. Off. . |
| 0 754 680 A1 | 1/1997 | European Pat. Off. . |

OTHER PUBLICATIONS

English Abstract for EP 0 754 680 A1 (Derwent Abstract No. 97–089242).

*Primary Examiner*—Shailendra Kumar
*Attorney, Agent, or Firm*—Finnegan, Henderson, Farabow, Garrett & Dunner, L.L.P.

[57] ABSTRACT

There are described benzoylguanidines of the formula I

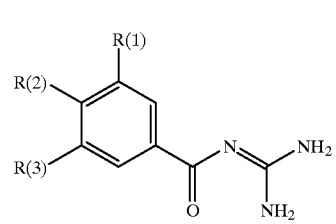

where R(1) is R(4)—SO$_m$, R(5)R(6)N—SO$_2$—; O$_p$—(CH$_2$)$_q$—(CF$_2$)$_r$—CF$_3$; —SR(10), —OR(10) or —CR(10)R(11)R(12); R(2) is —(CH$_2$)$_u$—(CF$_2$)$_t$—CF$_3$; R(3) is hydrogen or independently defined as R(1); and their pharmaceutically tolerable salts. They are obtained by reaction of a compound of the formula II

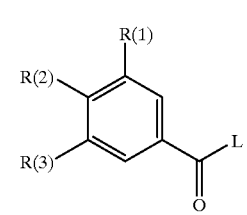

with guanidine.

They are compounds of outstanding activity on the cardiovascular system.

17 Claims, No Drawings

4-FLUOROALKYL-SUBSTITUTED BENZOYLGUANIDINES, PROCESS FOR THEIR PREPARATION, THEIR USE AS A MEDICAMENT OR DIAGNOSTIC, AND MEDICAMENT CONTAINING THEM

This application is a continuation of U.S. patent application Ser. No. 08/679,550, filed Jul. 12, 1996, now abandoned.

The invention relates to benzoylguanidines of the formula I

<img: structure of formula I showing benzene ring with R(1), R(2), R(3) substituents and C(=O)—N=C(NH_2)(NH_2) group> in which:
R(1) is $R(4)—SO_m$ or $R(5)R(6)N—SO_2—$;
  m is 1 or 2;
  R(4) and R(5)
    independently of one another are alkyl having 1, 2, 3, 4, 5, 6, 7 or 8 carbon atoms, alkenyl having 3, 4, 5 or 6 carbon atoms, $CF_3$ or $—C_nH_{2n}—R(7)$;
  n is zero, 1, 2, 3 or 4;
  R(6) is H or alkyl having 1, 2, 3 or 4 carbon atoms;
  R(7) is cycloalkyl having 3, 4, 5, 6, 7 or 8 carbon atoms, or phenyl which is unsubstituted or substituted by 1–3 substituents selected from the group consisting of F, Cl, $CF_3$, methyl, methoxy and $NR(8)R(9)$;
  R(8) and R(9)
    are H or alkyl having 1, 2, 3 or 4 carbon atoms;
or
  R(5) is also hydrogen;
or
  R(5) and R(6)
    together are 4 or 5 methylene groups, of which a $CH_2$ group can be replaced by oxygen, S, NH, N-$CH_3$ or N-benzyl;
or
R(1) is $—O_p—(CH_2)_q—(CF_2)_r—CF_3$;
  p is zero or 1;
  q is zero, 1 or 2;
  r is zero, 1, 2 or 3;
or
R(1) is $—SR(10)$, $—OR(10)$ or $—CR(10)R(11)R(12)$;
  R(10), R(11) and R(12)
    independently of one another are hydrogen, alkyl having 1, 2, 3, 4, 5, 6, 7 or 8 carbon atoms, $—C_sH_{2s}$-$(C_3$-$C_8)$-cycloalkyl or an aromatic system selected from the group consisting of pyridyl, pyrrolyl, quinolyl, isoquinolyl, imidazolyl or phenyl;
  s is zero, 1 or 2;
    where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is $—(CH_2)_u—(CF_2)_t—CF_3$;
  t is zero, 1, 2 or 3;
  u is zero or 1;
R(3) is hydrogen or independently defined as R(1);
and their pharmaceutically tolerable salts.

Preferred compounds of the formula I are those in which:
R(1) is $R(4)—SO_m$ or $R(5)R(6)N—SO_2—$;
  m is 1 or 2;
  R(4) and R(5)
    independently of one another are alkyl having 1, 2, 3, 4, 5, 6, 7 or 8 carbon atoms, $CF_3$ or $—C_nH_{2n}—R(7)$;
  n is zero, 1 or 2;
  R(6) is H or alkyl having 1, 2, 3 or 4 carbon atoms;
  R(7) is cycloalkyl having 3, 4, 5, 6, 7 or 8 carbon atoms;
or
R(1) is $—O_p—(CH_2)_q—(CF_2)_r—CF_3$;
  p is zero or 1;
  q is zero or 1;
  r is zero or 1;
or
R(1) is $—SR(10)$ or $—OR(10)$;
  R(10)
    is alkyl having 1, 2, 3, 4, 5, 6, 7 or 8 carbon atoms, $—C_sH_{2s}—(C_3$-$C_8)$-cycloalkyl or an aromatic system selected from the group consisting of pyridyl, pyrrolyl, quinolyl, isoquinolyl, imidazolyl or phenyl;
  s is zero, 1 or 2;
    where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;
R(2) is $—(CF_2)_t—CF_3$;
  t is zero or 1;
R(3) is hydrogen or independently defined as R(1); and their pharmaceutically tolerable salts.

Very particularly preferred compounds of the formula I are those in which:
R(1) is $R(4)—SO_2$ or $R(5)R(6)N—SO_2—$;
  R(4) and R(5)
    independently of one another are alkyl having 1, 2, 3, 4, 5, 6, 7 or 8 carbon atoms, $CF_3$ or cycloalkyl having 3, 4, 5, 6, 7 or 8 carbon atoms;
  R(6) is H or alkyl having 1, 2, 3 or 4 carbon atoms;
or
R(1) is $—O_p—(CF_2)_r—CF_3$;
  p is zero or 1;
  r is zero or 1;
or
R(1) is $—SR(10)$ or $—OR(10)$;
  R(10)
    is alkyl having 1, 2, 3, 4, 5, 6, 7 or 8 carbon atoms, $—C_sH_{2s}—(C_3$-$C_8)$-cycloalkyl or an aromatic system selected from the group consisting of pyridyl, pyrrolyl, quinolyl, isoquinolyl, imidazolyl or phenyl;
  s is zero, 1 or 2;
    where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is $CF_3$;
R(3) is hydrogen;
and their pharmaceutically tolerable salts.

Very specially preferred compounds of the formula I are those in which:
R(1) is $R(4)—SO_2$;
R(4) is alkyl having 1, 2, 3 or 4 carbon atoms or cycloalkyl having 5 or 6 carbon atoms;
or
R(1) is $—Op—(CF_2)_r—CF_3$;
p is zero or 1;
r is zero or 1;
or
R(1) is $—SR(10)$ or $—OR(10)$;
R(10)
is alkyl having 1, 2, 3 or 4 carbon atoms, $(C_5-C_6)$-cycloalkyl or an aromatic system selected from the group consisting of pyridyl, pyrrolyl, quinolyl, isoquinolyl, imidazolyl or phenyl,
where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;
R(2) is $CF_3$;
R(3) is hydrogen;
and their pharmaceutically tolerable salts.

If one of these substituents R(1) to R(12) contains one or more centers of asymmetry, these can have either the S or the R configuration. The compounds can exist as optical isomers, as diastereomers, as racemates or as mixtures thereof. The designated alkyl radicals can be straight-chain or branched.

The invention furthermore relates to a process for the preparation of the compounds I, which comprises reacting a compound of the formula II

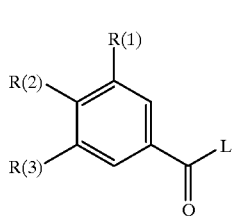

II in which R(1) to R(3) have the meaning indicated and L is a leaving group which can be readily nucleophilically substituted, with guanidine.

The activated acid derivatives of the formula II, in which L is an alkoxy group, preferably a methoxy group, a phenoxy group, a phenylthio, methylthio or 2-pyridylthio group or a nitrogen heterocycle, preferably 1-imidazolyl, are advantageously obtained in a manner known per se from the underlying carbonyl chlorides (formula II, L=Cl), which for their part in turn can be prepared in a manner known per se from the underlying carboxylic acids (formula II, L=OH), for example using thionyl chloride.

Beside the carbonyl chlorides of the formula II (L=Cl), further activated acid derivatives of the formula II can also be prepared directly from the underlying benzoic acid derivatives (formula II, L=OH) in a manner known per se, such as, for example, the methyl esters of the formula II where $L=OCH_3$ by treating with gaseous HCl in methanol, the imidazolides of the formula II by treating with carbonyldiimidazole [L=1-imidazolyl, Staab, Angew. Chem. Int. Ed. Eng. 1, 351–367 (1962)], the mixed anhydrides II using $Cl-COOC_2H_5$ or tosyl chloride in the presence of triethylamine in an inert solvent, and also the activation of benzoic acids using dicyclohexylcarbodiimide (DCC) or using O-[(cyano(ethoxycarbonyl)methylene)amino]-1,1,3,3-tetramethyluronium tetrafluoroborate ("TOTU") [Weiss and Krommer, Chemiker Zeitung 98, 817 (1974)]. A number of suitable methods for the preparation of activated carboxylic acid derivatives of the formula II are indicated under details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol, isopropanol or THF from 20° C. up to the boiling temperature of these solvents have proven suitable here in the reaction of the methyl benzoates (II, L=OMe) with guanidine. Most reactions of compounds II with salt-free guanidine were advantageously carried out in aprotic inert solvents such as THF, dimethoxyethane or dioxane. However, water can also be used in the reaction of II with guanidine using a base such as, for example, NaOH as a solvent.

If L=Cl, the reaction is advantageously carried out with addition of an acid scavenger, e.g. in the form of excess guanidine to bind the hydrohalic acid.

Some of the underlying benzoic acid derivatives of the formula II are known and described in the literature. The unknown compounds of the formula II can be prepared by methods known from the literature. The benzoic acids obtained are reacted to give compounds I according to the invention according to one of the process variants described above.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates, p-toluenesulfonates.

The compounds I are substituted acylguanidines. The most prominent representative of the acyl guanidines is the pyrazine derivative amiloride, which is used in therapy as a potassium-sparing diuretic. Numerous other compounds of the amiloride type are described in the literature, such as, for example, dimethylamiloride or ethylisopropylamiloride.

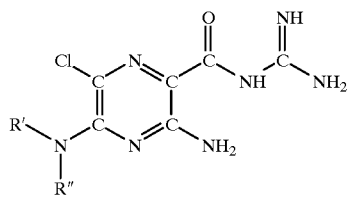

Amiloride: R',R"=H
Dimethylamiloride: $R',R"=CH_3$
Ethylisopropylamiloride: $R'=C_2H_5$, $R"=CH(CH_3)_2$ Moreover, investigations have been published which point to antiarrhythmic properties of amiloride (Circulation 79, 1257–63 (1989)). An obstacle to wide application as an antiarrhythmic, however, is that this effect is only weakly marked and occurs accompanied by a hypotensive and saluretic action and these side effects are undesirable in the treatment of cardiac arrhythmias.

Indications of antiarrhythmic properties of amiloride were also obtained in experiments on isolated animal hearts (Eur.

Heart J. 9 (suppl. 1): 1 67 (1 988) (book of abstracts)). For example, it was found in rat hearts that it was possible to completely suppress artificially induced ventricular fibrillation by means of amiloride. The abovementioned amiloride derivative ethylisopropylamiloride was even more potent than amiloride in this model.

U.S. Pat. No. 5,091,394 (HOE 89/F 288) and U.S. Pat. No. 5,373,024 (HOE 92/F 034) describe benzoylguanidines which, however, have no fluorinated alkyl substituents.

U.S. Pat. No. 3,780,027 claims acylguanidines which are structurally similar to the compounds of the formula I and are derived from commercially available loop diuretics, such as bumetanide, i.e. also do not concern fluorinated compounds. A potent salidiuretic activity is reported for these compounds.

German Offenlegungsschrift P 43 05 250.9 (HOE 93/F 054) already describes compounds which are related to the compounds according to the invention, but which in many respects still have unsatisfactory properties. In particular, among these there are still no compounds described having fluorine-containing substituents in the p-position.

The compounds according to the invention exhibit no undesirable and disadvantageous salidiuretic properties, but have very good antiarrhythmic properties, such as are important, for example, for the treatment of illnesses which occur in the case of oxygen deficiency symptoms. As a result of their pharmacological properties, the compounds I are outstandingly suitable as antiarrhythmic pharmaceuticals having a cardioprotective component for infarct prophylaxis and infarct treatment and also for the treatment of angina pectoris, where they also preventively inhibit or greatly reduce the pathophysiological processes in the formation of ischemically induced damage, in particular in the elicitation of ischemically induced cardiac arrhythmias. Because of their protective effects against pathological hypoxic and ischemic situations, the compounds of the formula I according to the invention can be used as a result of inhibition of the cellular $Na^+/H^+$ exchange mechanism as pharmaceuticals for the treatment of all acute or chronic damage caused by ischemia or primary or secondary illnesses induced thereby. This relates to their use as pharmaceuticals for surgical interventions, e.g. in organ transplantations, where the compounds can be used both for the protection of the organs in the donor before and during removal, for the protection of removed organs, for example, during treatment with or storage thereof in physiological bath fluids, and also during transfer to the body of the recipient. The compounds are also useful pharmaceuticals having protective activity when carrying out angioplastic surgical interventions, for example on the heart, and also on peripheral vessels. In accordance with their protective effect against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I are therefore suitable as useful therapeutics for illnesses in which cell proliferation is a primary or secondary cause, and can therefore be used as antiatherosclerotics, agents against diabetic late complications, carcinomatous disorders, fibrotic disorders such as pulmonary fibrosis, fibrosis of the liver or fibrosis of the kidney, organ hypertrophy and hyperplasia, in particular in prostate hyperplasia or prostate hypertrophy.

The compounds according to the invention are effective inhibitors of the cellular sodium proton antiporter ($Na^+/H^+$ exchanger), which is raised in numerous disorders (essential hypertension, atherosclerosis, diabetes etc.) even in those cells which are readily accessible to measurement, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative disorders etc. Moreover, the compounds of the formula I are suitable for preventive therapy for preventing the genesis of high blood pressure, for example of essential hypertension.

In this context, pharmaceuticals which contain a compound I can be administered orally, parenterally, intravenously, rectally or by inhalation, the preferred type of administration being dependent on the particular clinical picture of the disorder. In this context, the compounds I can be administered on their own or together with pharmaceutical auxiliaries, and indeed both in veterinary and in human medicine.

The auxiliaries which are suitable for the desired pharmaceutical formulation are familiar to the person skilled in the art on the basis of his expert knowledge. Beside solvents, gel formers, suppository bases, tablet auxiliaries, and other active compound excipients, it is possible to use, for example, antioxidants, dispersants, emulsifiers, antifoams, flavor corrigents, preservatives, solubilizers or colorants.

For a form for oral administration, the active compounds are mixed with the additives suitable for this purpose, such as excipients, stabilizers or inert diluents, and brought by means of the customary methods into the suitable administration forms, such as tablets, coated tablets, hard-gelatin capsules, aqueous, alcoholic or oily solutions. Inert excipients which can be used are, for example, gum arabic, magnesia, magnesium carbonate, potassium phosphate, lactose, glucose or starch, in particular maize starch. In this context, preparation can take place both as dry and moist granules. Suitable oily excipients or solvents are, for example, vegetable or animal oils, such as sunflower oil or fish liver oil.

For subcutaneous or intravenous administration, the active compounds, if desired with the substances customary for this purpose, such as solubilizers, emulsifiers or other auxiliaries, are brought into solution, suspension or emulsion. Possible solvents, for example, are: water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain yet other pharmaceutical auxiliaries such as surfactants, emulsifiers and stabilizers and also a propellant. Such a preparation customarily contains the active compound in a concentration of approximately 0.1 to 10, in particular of approximately 0.3 to 3,% by weight.

The dose of the active compound of the formula I to be administered and the frequency of administration depend on the potency and duration of action of the compounds used; additionally also on the nature and severity of the illness to be treated and on the sex, age, weight and individual responsiveness of the mammal to be treated.

On average, the daily dose of a compound of the formula I in the case of a patient of weight approximately 75 kg is at least 0.001 mg/kg, preferably 0.01 mg/kg, to at most 10 mg/kg, preferably 1 mg/kg, of body weight. In acute episodes of the illness, for example immediately after suffering a cardiac infarct, even higher and especially more frequent doses may also be necessary, e.g. up to 4 individual doses per day. In particular in the case of i.v. administration, for example in the case of an infarct patient in the intensive care unit, up to 200 mg per day may be necessary.

List of abbreviations:

| | |
|---|---|
| MeOH | Methanol |
| DMF | N,N-Dimethylformamide |
| RT | Room temperature |
| EA | Ethyl acetate (EtOAc) |
| M.p | Melting point |
| THF | Tetrahydrofuran |
| eq. | Equivalent |

Experimental Section

General procedure for the preparation of benzoylguanidines (I)

Variant A: from benzoic acids (II, L=OH)

1.0 eq. of the benzoic acid derivative of the formula II is dissolved or suspended in anhydrous THF (5 ml/mmol) and then treated with 1.1 eq. of carbonyldiimidazole. After stirring for 2 hours at RT, 5.0 eq. of guanidine are introduced into the reaction solution. After stirring overnight, the THF is distilled off under reduced pressure (Rotavapor), treated with water and adjusted to pH 6 to 7 with 2N HCl, and the corresponding benzoylguanidine (formula 1) is filtered off. The benzoylguanidine thus obtained can be converted into the corresponding salts by treating with aqueous, methanolic or ethereal hydrochloric acid or other pharmacologically tolerable acids.

General procedure for the preparation of benzoylguanidines (I)

Variant B: from alkyl benzoates (II, L=O-Alkyl)

1.0 eq. of the alkyl benzoate of the formula 11 and 5.0 eq. of guanidine (free base) are dissolved in isopropanol or suspended in THF and heated to reflux (typical reaction time 2 to 5 h) until conversion is complete (thin-layer checking). The solvent is distilled off under reduced pressure (Rotavapor), the residue is taken up in EA and the solution is washed 3 times with $NaHCO_3$ solution. It is dried over $Na_2SO_4$, the solvent is distilled off in vacuo and the residue is chromatographed on silica gel using a suitable eluent, e.g. EA/MeOH 5:1.

(For salt formation compare variant A)

EXAMPLE 1

3-Methylsulfonyl-4-trifluoromethylbenzoylguanidine hydrochloride:

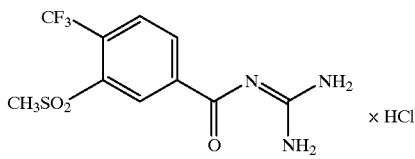

Colorless crystals, m.p. 236° C.
Synthetic route:
a) Methyl 3-methylsulfonyl-4-trifluoromethylbenzoate from methyl 4-bromo-3-methylsulfonylbenzoate by heating to 90° C. with potassium trifluoroacetate in NMP in the presence of copper(1) iodide.
b) 3-Methylsulfonyl-4-trifluoromethylbenzoylguanidine hydrochloride by general procedure, Variant B.

What is claimed is:
1. A benzoylguanidine of the formula I

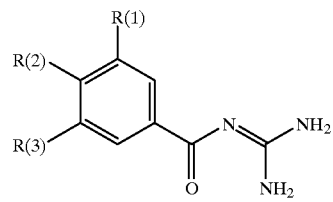

in which:
R(1) is R(4)—$SO_m$ or R(5)R(6)N—$SO_2$—;
  m is 1 or 2;
  R(4) and R(5)
    independently of one another are alkyl having 1, 2, 3, 4, 5, 6, 7 or 8 carbon atoms, alkenyl having 3, 4, 5 or 6 carbon atoms, $CF_3$ or —$C_nH_{2n}$—R(7);
  n is zero, 1, 2, 3 or 4;
  R(6) is H or alkyl having 1, 2, 3 or 4 carbon atoms;
  R(7) is cycloalkyl having 3, 4, 5, 6, 7 or 8 carbon atoms, or phenyl which is unsubstituted or substituted by 1–3 substituents selected from the group consisting of F, Cl, $CF_3$, methyl, methoxy and NR(8)R(9);
    R(8) and R(9) independently of one another
      are H or alkyl having 1, 2, 3 or 4 carbon atoms;
  or
  R(5) is also hydrogen;
  or
  R(5) and R(6)
    together are 4 or 5 methylene groups, of which a $CH_2$ group can be replaced by oxygen, S, NH, N—$CH_3$ or N-benzyl;
or
R(1) is —SR(10); wherein
  R(10)
    is hydrogen, alkyl having 1, 2, 3, 4, 5, 6, 7 or 8 carbon atoms, —$C_sH_{2s}$—($C_3$-$C_8$)-cycloalkyl or an aromatic system selected from the group consisting of pyridyl, pyrrolyl, quinolyl, isoquinolyl, imidazolyl or phenyl;
  s is zero, 1 or 2;

where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is —$(CH_2)_u$—$(CF_2)_t$—$CF_3$;

t is zero, 1, 2 or 3;

u is zero or 1;

R(3) is hydrogen or independently defined as R(1);

or a pharmaceutically tolerable salt thereof.

2. A compound or salt of the formula I as claimed in claim 1, wherein:

R(1) is R(4)—$SO_m$ or R(5)R(6)N—$SO_2$—;

m is 1 or 2;

R(4) and R(5)

independently of one another are alkyl having 1, 2, 3, 4, 5, 6, 7 or 8 carbon atoms, $CF_3$ or —$C_nH_{2n}$—R(7);

n is zero, 1 or 2;

R(6) is H or alkyl having 1, 2, 3 or 4 carbon atoms;

R(7) is cycloalkyl having 3, 4, 5, 6, 7 or 8 carbon atoms;

or

R(1) is —SR(10); wherein

R(10)

is alkyl having 1, 2, 3, 4, 5, 6, 7 or 8 carbon atoms, —$C_sH_{2s}$—$(C_3–C_8)$—cycloalkyl or an aromatic system selected from the group consisting of pyridyl, pyrrolyl, quinolyl, isoquinolyl, imidazolyl or phenyl;

s is zero, 1 or 2;

where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is —$(CF_2)_t$—$CF_3$;

t is zero or 1; and

R(3) is hydrogen or independently defined as R(1).

3. A compound or salt of the formula I as claimed in claim 1, wherein:

R(1) is R(4)—$SO_2$ or R(5)R(6)N—$SO_2$—;

R(4) and R(5)

independently of one another are alkyl having 1, 2, 3, 4, 5, 6, 7 or 8 carbon atoms, $CF_3$ or cycloalkyl having 3, 4, 5, 6, 7 or 8 carbon atoms; R(6) is H or alkyl having 1, 2, 3 or 4 carbon atoms;

or

R(1) is —SR(10); wherein

R(10)

is alkyl having 1, 2, 3, 4, 5, 6, 7 or 8 carbon atoms, —$C_sH_{2s}$—$(C_3–C_8)$—cycloalkyl or an aromatic system selected from the group consisting of pyridyl, pyrrolyl, quinolyl, isoquinolyl, imidazolyl or phenyl;

s is zero, 1 or 2;

where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is $CF_3$; and

R(3) is hydrogen.

4. A compound of the formula I as claimed in claim 1, wherein:

R(1) is R(4)—$SO_2$;

R(4) is alkyl having 1, 2, 3 or 4 carbon atoms or cycloalkyl having 5 or 6 carbon atoms;

or

R(1) is —SR(10); wherein

R(10)

is alkyl having 1, 2, 3 or 4 carbon atoms, $(C_5–C_6)$-cycloalkyl or an aromatic system selected from the group consisting of pyridyl, pyrrolyl, quinolyl, isoquinolyl, imidazolyl or phenyl, where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is $CF_3$; and

R(3) is hydrogen.

5. A process for the preparation of a compound of the formula I as claimed in claim 1, which comprises reacting a compound of the formula II

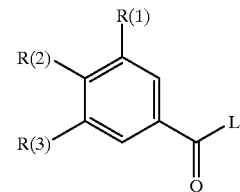

in which R(1) to R(3) have the meaning indicated in claim 1 and L is a leaving group which can be readily nucleophilically substituted, with guanidine.

6. A method of treating arrhythmia in a patient in need thereof comprising administering to the patient a therapeutically effective amount of a compound according to claim 1.

7. A method of treating or preventing cardiac infarct in a patient in need thereof comprising administering to the patient a therapeutically effective amount of a compound according to claim 1.

8. A method of treating or preventing angina pectoris in a patient in need thereof comprising administering to the patient a therapeutically effective amount of a compound according to claim 1.

9. A method of treating or preventing cardiac ischemia in a patient in need thereof comprising administering to the patient a therapeutically effective amount of a compound according to claim 1.

10. A method of treating or preventing neurological ischemia or stroke in a patient in need thereof comprising administering to the patient a therapeutically effective amount of a compound according to claim 1.

11. A method of treating shock in a patient in need thereof comprising administering to the patient a therapeutically effective amount of a compound according to claim 1.

12. A method for the preservation and storage of an organ for surgical transplant comprising administering to the organ a therapeutically effective amount of a compound according to claim 1.

13. A method of treating or preventing ischemic conditions of peripheral organs and members in a patient in need thereof comprising administering to the patient a therapeutically effective amount of a compound according to claim 1.

14. A method for the treatment of an illness in which cell proliferation is a primary or secondary cause such as atheroscleroses, late complications of diabetes, carcinomatous disorders, fibrotic disorders such as pulmonary fibrosis, fibrosis of the liver or fibrosis of the kidney and prostate hyperplasia in a patient in need thereof comprising administering to the patient a therapeutically effective amount of a compound according to claim 1.

15. A method for inhibiting the $Na^+/H^+$ exchanger in a patient in need thereof comprising administering to the patient a therapeutically effective amount of a compound according to claim 1.

16. A method for diagnosing hypertension or a proliferative disorder comprising utilizing a compound according to claim 1 as a diagnostic.

17. A pharmaceutical composition comprising a compound of claim 1 and an acceptable pharmaceutical carrier or diluent.

* * * * *